United States Patent
Paz et al.

(10) Patent No.: US 8,747,420 B2
(45) Date of Patent: Jun. 10, 2014

(54) EXTRACTING DEVICE FOR SURGICAL FASTENERS

(75) Inventors: Adrian Paz, Petach Tikva (IL); Gilad Heftman, Kibbutz Ein Gev (IL); Eitan Hod, Zichron Ya'akov (IL)

(73) Assignee: I.B.I Israel Biomedical Innovations Ltd., Kibbutz Haogen (IL)

( * ) Notice: Subject to any disclaimer, the term of this patent is extended or adjusted under 35 U.S.C. 154(b) by 488 days.

(21) Appl. No.: 12/084,317

(22) PCT Filed: Nov. 2, 2006

(86) PCT No.: PCT/IL2006/001273
§ 371 (c)(1),
(2), (4) Date: Apr. 30, 2008

(87) PCT Pub. No.: WO2007/052276
PCT Pub. Date: May 10, 2007

(65) Prior Publication Data
US 2009/0264900 A1    Oct. 22, 2009

Related U.S. Application Data

(60) Provisional application No. 60/732,101, filed on Nov. 2, 2005.

(51) Int. Cl.
*A61B 17/10* (2006.01)

(52) U.S. Cl.
USPC ............................................. 606/138

(58) Field of Classification Search
USPC .................. 606/138, 151, 157, 228
See application file for complete search history.

(56) References Cited

U.S. PATENT DOCUMENTS

| | | | |
|---|---|---|---|
| 5,222,951 A | 6/1993 | Abidin et al. | |
| 5,236,435 A | 8/1993 | Sewell, Jr. | |
| 5,312,338 A | 5/1994 | Nelson et al. | |
| 5,649,931 A | 7/1997 | Bryant et al. | |
| 5,820,628 A | 10/1998 | Middleman et al. | |
| 5,948,002 A * | 9/1999 | Bonutti | 606/232 |
| 6,066,143 A | 5/2000 | Lane | |
| 7,322,992 B2 * | 1/2008 | Trout et al. | 606/138 |
| 7,563,267 B2 * | 7/2009 | Goldfarb et al. | 606/151 |
| 8,529,583 B1 * | 9/2013 | Golden et al. | 606/138 |
| 2003/0187470 A1 * | 10/2003 | Chelak et al. | 606/182 |
| 2004/0059348 A1 | 3/2004 | Geske et al. | |
| 2004/0158257 A1 | 8/2004 | Bonati et al. | |

FOREIGN PATENT DOCUMENTS

| | | |
|---|---|---|
| EP | 0 707 829 A1 | 4/1996 |
| EP | 1 661 527 A1 | 5/2006 |
| JP | 2004-160177 A | 6/2004 |
| WO | 96/16602 A1 | 6/1996 |
| WO | 2007/004228 A1 | 1/2007 |

OTHER PUBLICATIONS

International Search Report of related International Application No. PCT/IL2006/001273, mailed Feb. 2, 2007.

* cited by examiner

*Primary Examiner* — Melanie Tyson
(74) *Attorney, Agent, or Firm* — Vorys, Sater, Seymour and Pease LLP; Susanne M. Hopkins; William L. Klima (57) ABSTRACT

The application provides a device (2) for extracting from a body tissue surgical fasteners (20) having a crown, a baseplate and prongs extending from the crown to the baseplate. The device includes a shaft having a lumen with a cross-sectional shape and dimensions to allow the crown to enter the lumen while preventing the baseplate from entering the lumen.

2 Claims, 9 Drawing Sheets

EXTRACTING DEVICE FOR SURGICAL FASTENERS

This is a National Phase Application filed under 35 U.S.C. 371 as a national stage of PCT/IL2006/001273, filed on Nov. 2, 2006, an application claiming the benefit under 35 U.S.C. 119(e) of U.S. Provisional Application No. 60/732,101, filed on Nov. 2, 2005, the entire content of each of which is hereby incorporated by reference in its entirety.

FIELD OF THE INVENTION

This invention relates to surgical devices, and more particularly to devices related to surgical fastening.

BACKGROUND OF THE INVENTION

Surgical anchors are used instead of surgical suturing, which is often both time consuming and inconvenient, in order to join two tissue locations. A surgeon can often use a stapling apparatus to implant an anchor into a body tissue and thus accomplish in a few seconds, what would take a much longer time to suture. A surgical anchor is used, for example in inguinal hernia surgery to fasten polypropylene mesh to the abdominal wall in order to reinforce the abdominal wall.

Surgical fasteners are known in the form of a staple in which a pair of prongs extends from a crown. In some applications, the body tissue is accessible from two opposite direction so that a deployment device may be used having an anvil that is used to bend the prongs towards each other after the prongs have penetrated through the tissue. In applications where access to the tissue is from one direction only, deployment device is used that delivers a force to the crown that deforms the crown and thus causes the prongs to project towards and grasp the tissue.

Applicant's co-pending application PCT/IL2006/000783 filed on Jul. 6, 2006, the contents of which are included herein in their entirety by reference, discloses surgical fasteners having two or more prongs, each of which is connected to a crown by hinge. In an undeployed configuration of the fastener, the tips of the prongs are inserted into slots in a base plate. The crown is thus separated from the baseplate in the undeployed configuration of the fastener by the length of the prongs. This configuration is stabilized by an engagement between the prongs and the baseplate, for example, by friction between the prongs and slot edges or by filling the slots with adhesive, glue or by a plug of softer material such as a biodegradable material. Deployment of such a fastener involves positioning the fastener at the site of a tissue surface where it is to be deployed and urging the crown towards the baseplate. As the prongs pass through the slots, they enter the tissue while the force applied to the prongs by the slot edges causes them to rotate at the hinges and splay radially outward from the crown so as to become embedded in the tissue. Only the prongs penetrate into the tissue, while the crown and baseplate become attach to the tissue surface without penetrating into it. The fastener may be used to attach a graft or a mesh to a body tissue.

As further disclosed in PCT/IL2006/000783, the above described fastener may become locked in its deployed configuration. Locking of the fastener in its deployed configuration allows the fastener to better withstand forces acting on it within the tissue and thus prevents inadvertent release of the fastener from the body tissue. The locking is accomplished by means of an engagement between components of the fastener that increases the force necessary to bend the extended prongs of the deployed fastener closer to the longitudinal axis of the fastener compared to situation in which locking means are not provided. The locking may be due to an engagement between the prongs and the crown, the prongs and the baseplate, or the crown and the baseplate. For example, the locking may result from increased friction between the prongs and slots due to a region along the length of the prongs of increased width or thickness that enters the slot during deployment, so that the prong becomes jammed in the slot. The prongs may be locked in the deployed configuration by engagement of a tongue extending from each slot of the second element into an opening in the prong. Alternatively, a tongue in the prong may engage an opening in the second element.

SUMMARY OF THE INVENTION

In its first aspect, the present invention provides an extracting device for extracting a deployed surgical fastener from a body tissue. The extracting device of the invention is used to extract surgical fasteners having a crown and a baseplate, for example, surgical fasteners as disclosed in PCT/IL2006/000783. The extracting device may be used for surgical fasteners that become locked in the deployed configuration.

The extraction device of the invention has a slender shaft. At least a distal portion of the shaft is hollow. In accordance with the invention, the hollow distal portion has a lumen having a cross-sectional shape and dimensions that allow the crown to enter lumen while preventing the baseplate from entering the lumen. As the crown is pulled into the distal portion, the baseplate becomes immobilized at the distal end of the shaft causing the crown and baseplate to be pulled apart.

In one preferred embodiment, the extracting device of the invention has a slender shaft that may be stiff or flexible, as required in any application. The shaft comprises an internal rod that terminates at its distal end in a hook. The rod is slidable inside a hollow sheath between a retracted position in which the hook is contained within the distal end of the sheath and an extended position in which the hook extends beyond the distal end of the sheath.

To extract a deployed surgical fastener the rod is brought to its extended configuration with the hook extending beyond the distal end of the sheath. The hook is then inserted between the crown and baseplate of the deployed fastener and the rod is made to move towards its retracted position pulling the fastener towards the distal end of the sheath. The sheath has an interior lumen that has a cross-sectional shape and dimensions that allow the crown to enter the lumen, while the baseplate is prevented from entering the lumen. Thus, as the hook enters the interior of the sheath, the crown is pulled by the hook into the interior of the sheath while movement of the baseplate is arrested with the baseplate in contact with the distal end of the sheath. As the crown moves away from the baseplate, the prongs slide through the slots until the tips of the prongs are at or near the tissue surface. The extraction device can then be removed from the body together with the un-deployed fastener.

In another preferred embodiment, the extracting device has a shaft having at its distal end a hollow tubular unit. The tubular unit includes a hollow cylindrical element having a longitudinal groove along its length. The cylindrical element has a lumen having a cross-sectional shape and dimensions that allow the crown to enter the lumen, while the baseplate is prevented from entering the lumen. This embodiment is used when a filament has been inserted between the crown and the baseplate of the deployed fastener. The filament is inserted into the longitudinal groove and grasped in the groove. The filament is then pulled away from the tissue surface in which the fastener is deployed. As the filament is pulled away, the crown of the fastener enters into the lumen of the cylindrical element, while movement of the baseplate is arrested when the baseplate contacts the distal end of the cylindrical element. As the crown moves away from the baseplate, the prongs slide through the slots until the tips of the prongs are at or near the tissue surface. The extraction device, with the fastener is then removed from the body.

In its second aspect, the invention provides a method for removing a deployed surgical fastener having a crown and baseplate. In accordance with this aspect of the invention, a surgical extraction device of the invention is used to extract the fastener by bringing the rod to its extended position and inserting the hook between the crown and baseplate of the deployed fastener. The rod is then brought to its retracted position to pull the fastener towards the distal end of the sheath. As the crown moves away from the baseplate, the prongs slide through the slots until the tips of the prongs are at or near the tissue surface. The extraction device can then be removed from the body together with the undeployed fastener.

Thus, in its first aspect, the invention provides a device for extracting a surgical fastener, the surgical fastener having a crown, a baseplate and prongs extending from the crown, the surgical fastener having an undeployed configuration in which the crown is separated from the baseplate by a first distance and a deployed configuration in which the crown is separated from the baseplate by a second distance that is less than the first distance, the device comprising:
(a) a shaft having a proximal end and a distal end, at least a distal portion of the shaft having a lumen with a cross-sectional shape and dimensions to allow the crown to enter the lumen while preventing the baseplate from entering the lumen.

In its second aspect, the invention provides a method for extracting a deployed surgical fastener from a body tissue, the surgical fastener having a crown, a baseplate and prongs extending from the crown, the surgical fastener having an undeployed configuration in which the crown is separated from the baseplate by a first distance and a deployed configuration in which the crown is separated from the baseplate by a second distance that is less than the first distance;
the method comprising:
(a) providing an extracting device, the extracting device comprising:
   i) a shaft having a proximal end and a distal end, at least a distal portion of the shaft having a lumen with a cross-sectional shape and dimensions to allow the crown to enter the lumen while preventing the baseplate from entering the lumen; and
(b) Introducing the crown into the hollow portion while preventing the advancement of the baseplate by the distal part of the hollow shaft.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 1 shows a device for extracting a surgical fastener in accordance with one embodiment of the invention, in a side view (FIG. 1a), a longitudinal section with the hook retracted (FIG. 1b), and a longitudinal section with the hook extended (FIG. 1c);

FIG. 3 shows the fastener of FIG. 2 at a tissue surface in an undeployed configuration (FIG. 3a) and in a deployed configuration (FIG. 3b);

FIG. 5 shows a device for extracting a surgical fastener in accordance with another embodiment of the invention, with the ring element in register with the longitudinal groove (FIG. 5a) and with the ring element out of register with the longitudinal groove (FIG. 5b);

FIG. 6 shows a surgical fastener having a crown and a baseplate in an undeployed configuration (FIG. 6a) and in a deployed configuration (FIG. 6b) with a filament passing between the crown and the baseplate.

DETAILED DESCRIPTION OF EXEMPLARY EMBODIMENTS

Figures 1A, 1B, 1C:
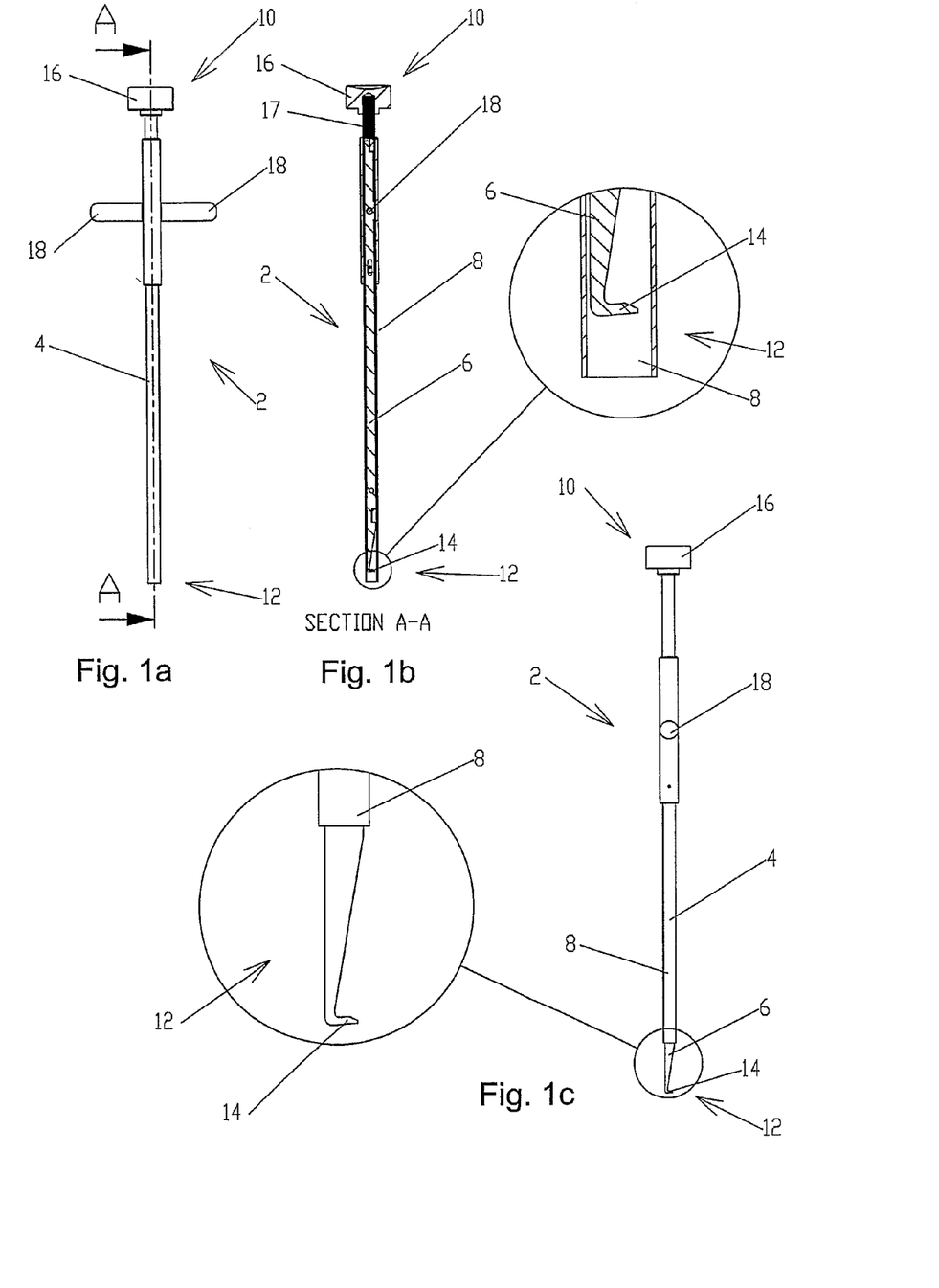

FIG. 1 shows an extracting device 2 for extracting a surgical fastener in accordance with one embodiment of the invention. The extracting device 2 is shown in a side view in FIGS. 1a and 1c, and in a longitudinal sectional view in FIG. 1b. The extracting device 2 has a proximal end, 10 and a distal end 12. The extracting device 2 has a slender shaft 4 that may be stiff or flexible, as required in any application. The shaft 4 comprises an internal rod 6 surrounded by an external sheath 8. The rod 6 terminates at its distal end in a hook 14. The rod 6 is slidable inside the sheath between a retracted position shown in FIGS. 1a and 1b in which the hook 14 is contained within the distal end of the sheath 8 and an extended position shown in FIG. 1c in which the hook extends beyond the distal end of the sheath 8. The rod 6 is spring 17 biased in its extended position by means of a spring 17. The rod 6 is brought to its retracted position by pulling a handle 18 in a proximal direction towards a knob 16. The handle 18 is attached to the proximal end of the rod 6, and as the handle is pulled, the spring 17 is compressed. The palm of a user's hand is applied to the knob 16 and the user's fingers are hooked on the handle 18. The user then squeezes the handle towards the knob. When the handle is released, the rod reverts to its extended position under the influence of the spring 17

As shown in FIGS. 1b and 1c (enlarged views), the hook 14 has a flat top surface and a flat bottom surface, the top and bottom surfaces being substantially perpendicular to a direction of motion of the hook when the hook moves between the retracted position and the extended position.

Figure 2:
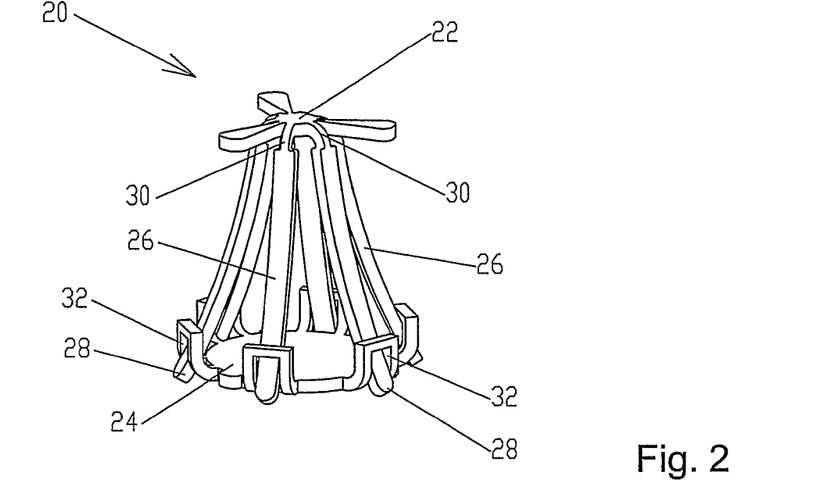
FIG. 2 shows a surgical fastener having a crown and a baseplate in an undeployed configuration.

FIG. 2 shows an exemplary prior art surgical fastener 20 having a crown 22 and a baseplate 24 in its undeployed configuration. A number of prongs 26 extend from the crown. The prongs 26 are bent at hinge regions 30. Each of the prongs 26 terminates in a tip 28 that is inserted into a slot 32 in the baseplate.

Figure 3A:
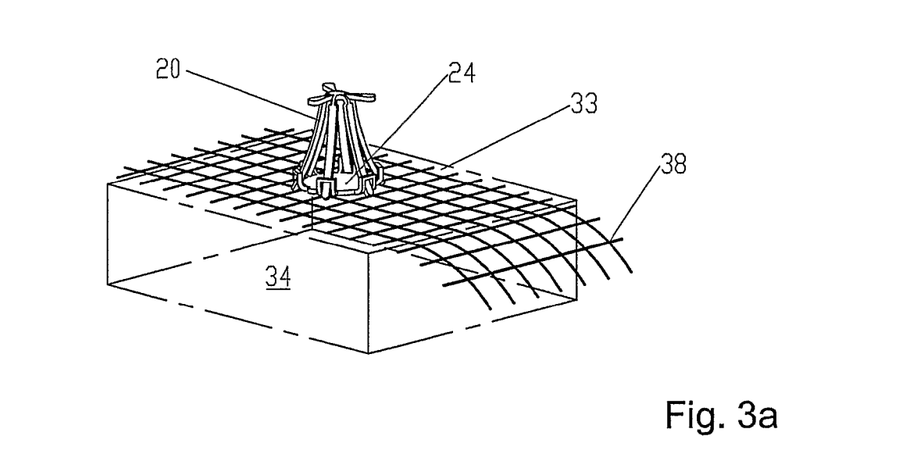
Figure 3B:
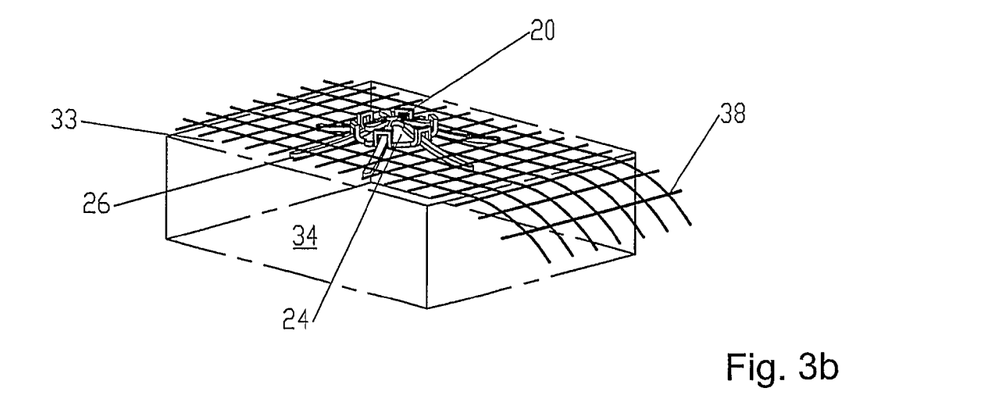

FIG. 3 shows the fastener 20 after delivery to a body tissue site. As shown in FIG. 3a, the fastener 20 has been delivered to a surface 33 of a body tissue 34, with the baseplate 24 and prong tips adjacent to the tissue surface 33. The body tissue 34 is indicated in FIG. 3 by broken lines. A surgical material 38 such as a sheet or mesh-like structure may first be applied to the tissue surface 33. Using a deployment device (not shown), the crown 22 of the fastener 20 is displaced towards the base plate 24. As the crown 22 approaches the baseplate 24, the prongs 26 enter the tissue 34 and splay radially outward inside the tissue, as shown in FIG. 3b. The prongs 26 become embedded in the tissue 34, so that the fastener 20 is immobilized at the tissue surface 33 with the crown 22 and the baseplate 24 on the tissue surface 33. The surgical material 38, if present has thus been grasped at the tissue surface. The fastener 20 may become locked in the deployed configuration.

Figures 4A, 4B, 4C, 4D:
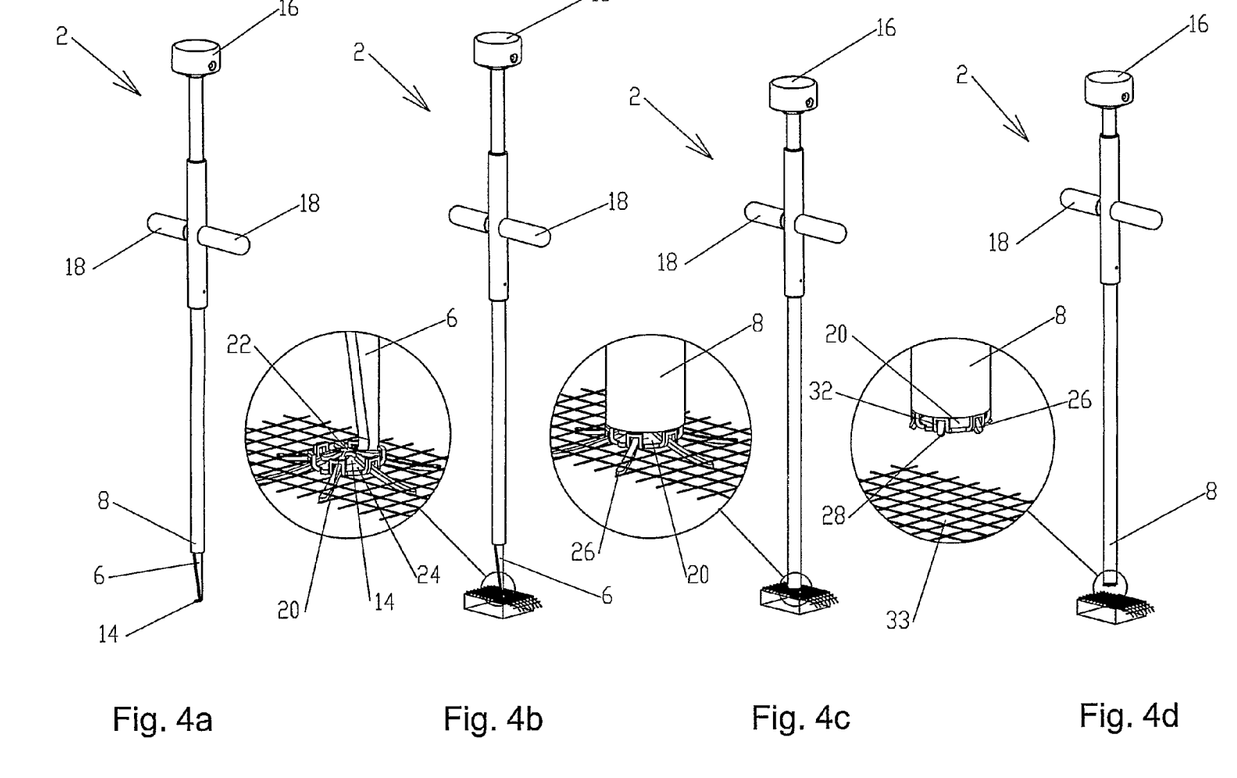
FIGS. 4a to FIG. 4d show use of the device of FIG. 1 for removing a surgical fastener having a baseplate and crown.

FIG. 4 shows use of the extracting device 2 to extract the surgical fastener 20 after its deployment as shown in FIG. 3b. This is by way of example only, and the extracting device of the invention may be used to extract any surgical fastener having a crown and baseplate. FIG. 4a shows the extracting device 2 with the rod 6 in its extended configuration so that the hook 14 extends beyond the distal end of the sheath 8. In FIG. 4b, the hook 14 has been inserted between the crown 22 and the baseplate 24. As the handle 18 is pulled (FIG. 4c), the hook 14 moves towards its retracted position, pulling the crown of the fastener 20 towards the distal end of the sheath 8. The sheath 8 has an inner lumen having a cross-sectional shape and dimensions that allow the crown to enter the lumen, while the baseplate is prevented from entering the lumen. Thus, as the hook 14 enters the lumen of the sheath, the crown 22 is pulled by the hook 14 into the lumen of the sheath 8 while movement of the baseplate 24 is arrested when the baseplate 24 contacts the distal end of the sheath 8, as shown in FIG. 4d. As the crown 22 moves away from the baseplate 24, the prongs 26 slide through the slots 32 until the tips 28 of the prongs 26 are at or near the tissue surface 33. With the handle 18 remaining pulled towards the knob 16 so that the fastener 20 is firmly held at the distal end of the sheath 8 by the hook 14, the extraction device 2 is removed from the body.

Figure 5A:
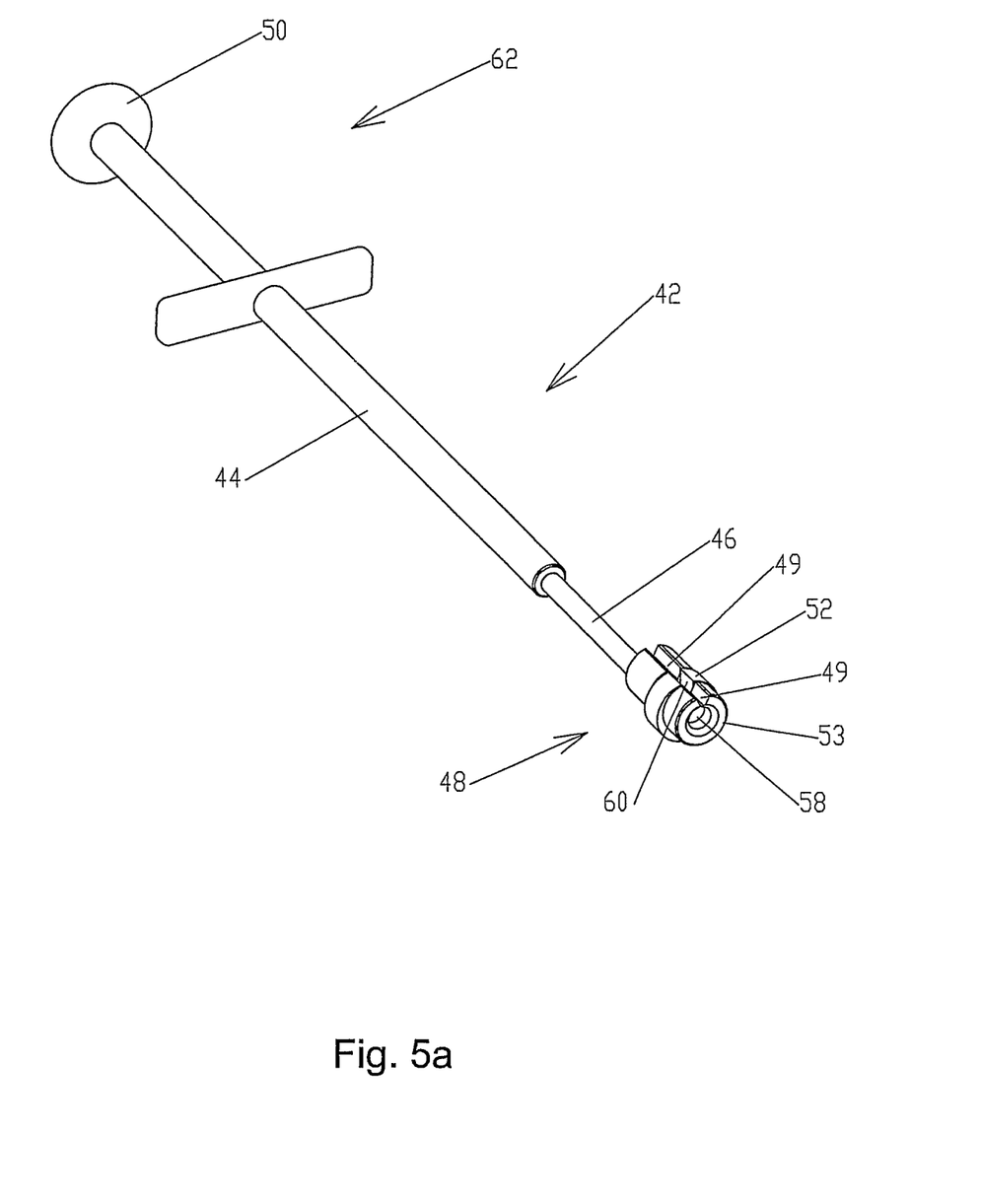
Figure 5B:
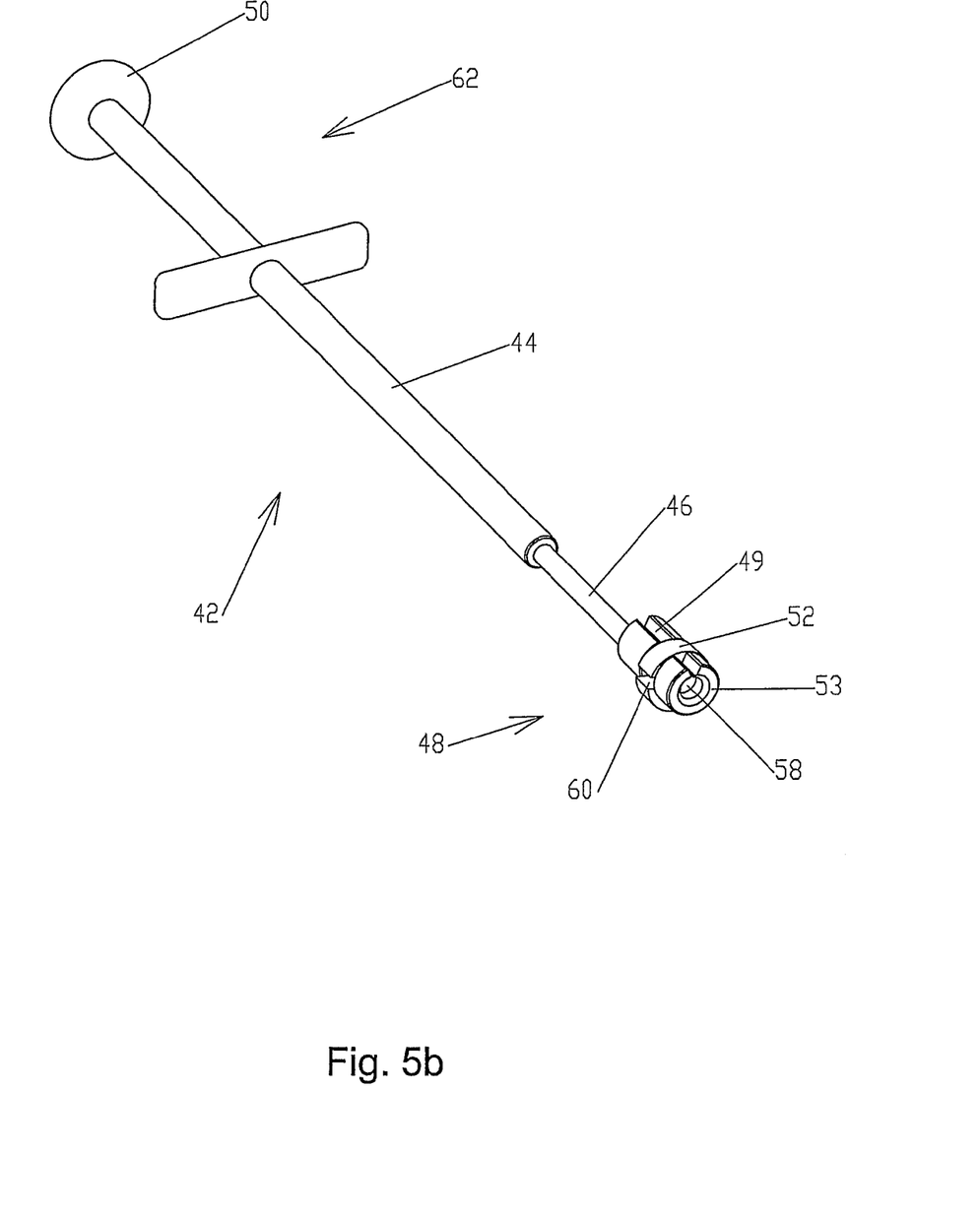

FIG. 5 shows an extracting device 42 for extracting a surgical fastener in accordance with another embodiment of the invention. The extracting device 42 has a proximal end 50 and a distal end 53. The extracting device 42 has a shaft 44 that may be stiff or flexible, as required in any application. The shaft 44 may have a uniform diameter along its length, or may have a thinner portion 46 at its distal end as shown in FIG. 5. The shaft 44 has at its distal end a hollow tubular unit 48 The tubular unit 48 includes a hollow cylindrical element 58 having a longitudinal groove 49 along its length. The tubular unit 48 is rigidly fixed to the distal end of the shaft 44 and has a lumen having a cross-sectional shape and dimensions that allow the crown to enter the lumen, while the baseplate is prevented from entering the lumen. The tubular unit 48 also includes a ring element 52. The ring element 52 incompletely surrounds the cylindrical element 58 and thus has a gap 60 between its ends. The ring element 52 is rotatable about the cylindrical element 58 from a position in which the gap 60 is in register with the longitudinal groove 49, as shown in FIG. 5a, and a position in which the gap 60 is completely out of register with the groove 49, as shown in FIG. 5b. The extraction device also includes a handle 62 for manipulating the device during extraction of a deployed surgical fastener, as explained below.

Figure 6A:
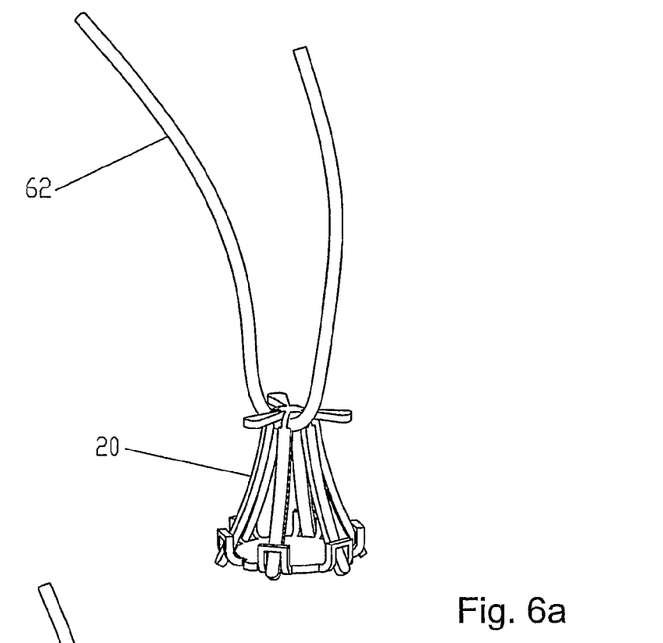

FIG. 6 shows again the surgical fastener 20 in its undeployed configuration. In FIG. 6a, a filament 62 has been inserted between the crown 22 and the baseplate 24. After deployment of the fastener 20, at a body tissue site, as explained above, the filament becomes pinched and immobilized between the crown 22 and the baseplate 24, as shown in FIG. 6b.

Figure 6B:
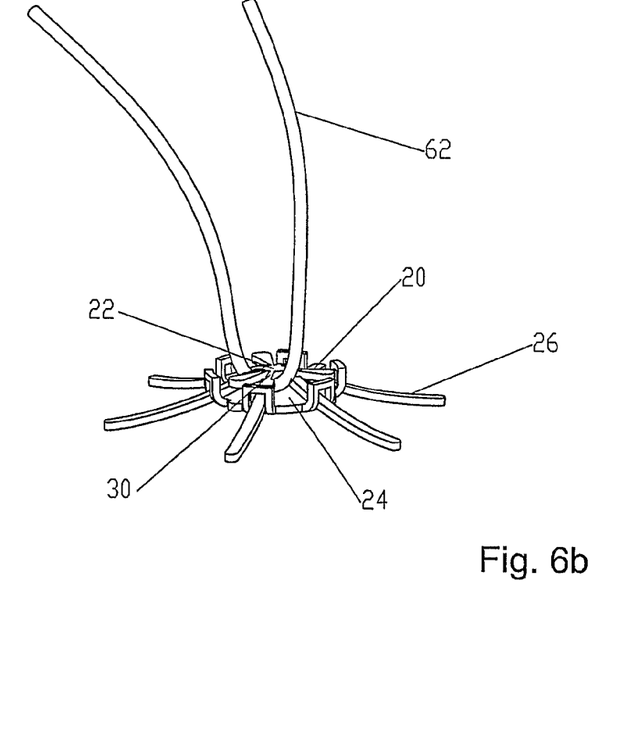
Figure 7A:
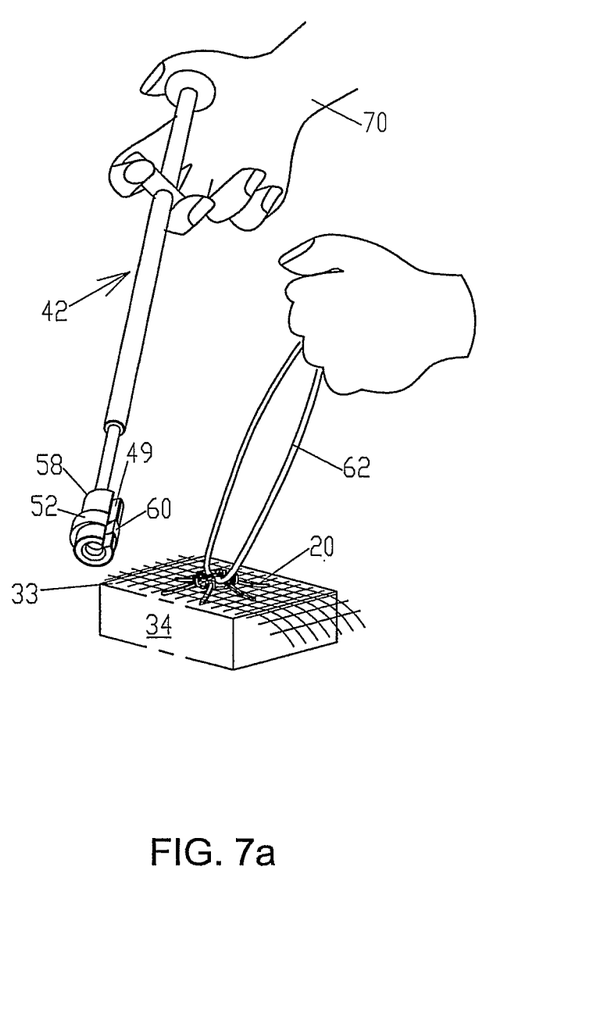
FIGS. 7a to 7e show use of the device of FIG. 5 for removing a surgical fastener having a crown and a baseplate and a filament passing between the crown and the baseplate.
Figure 7B:
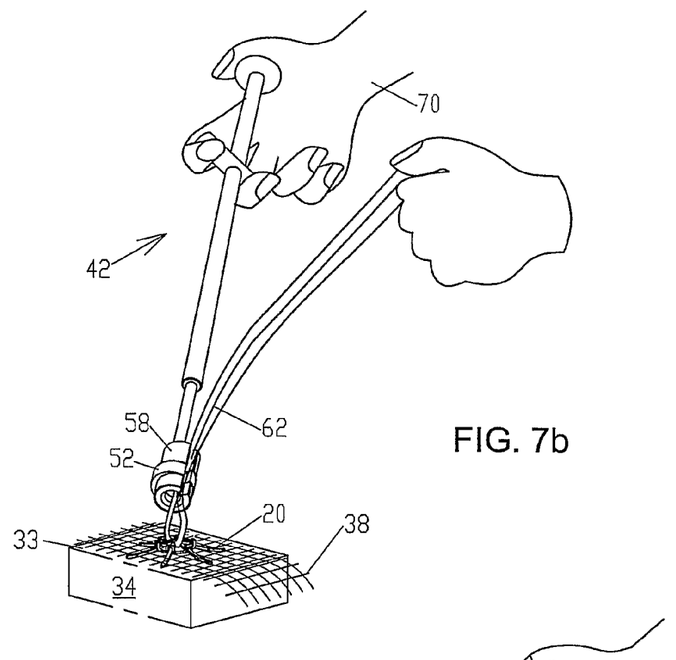
Figure 7C:
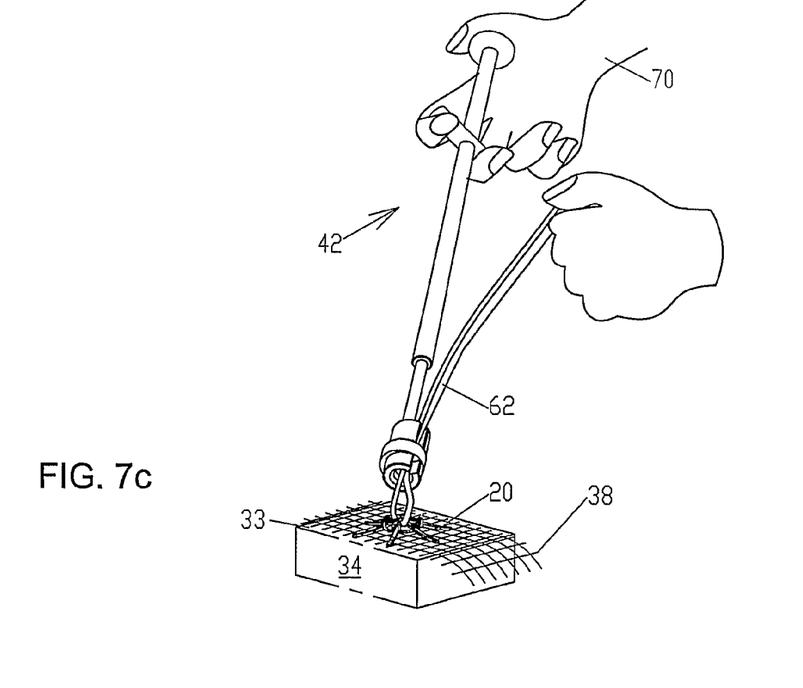
Figure 7D:
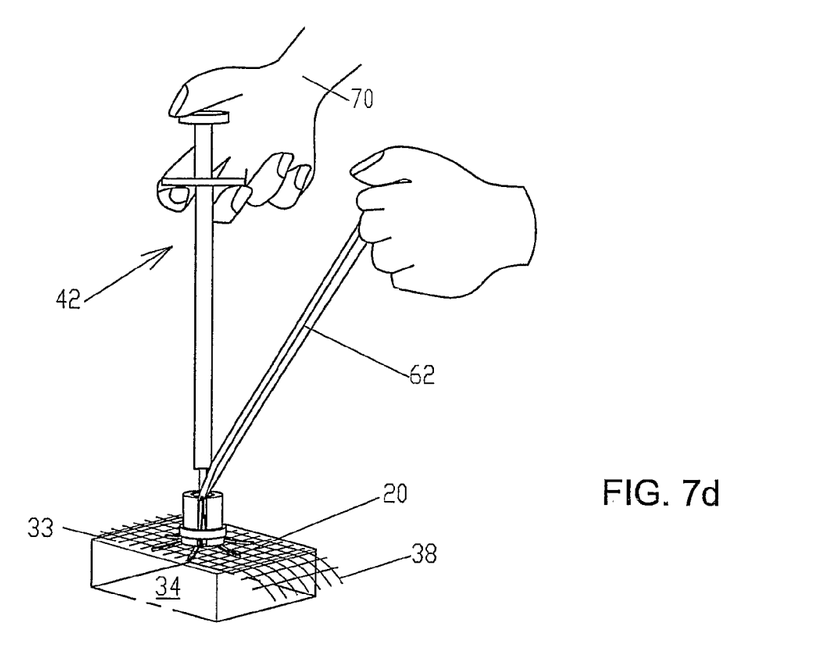
Figure 7E:
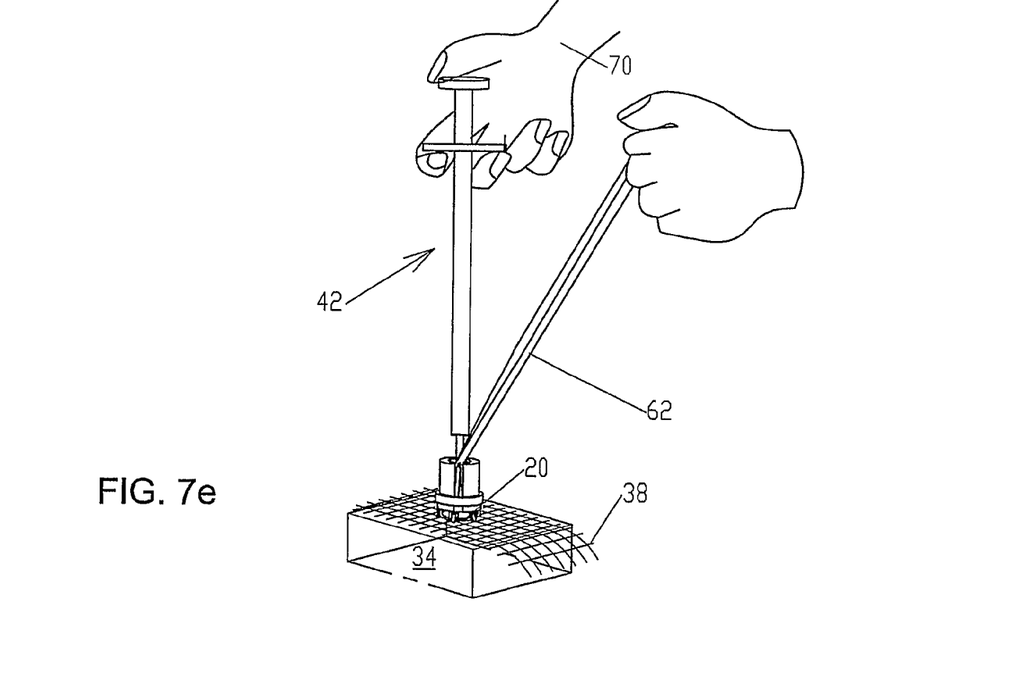

FIG. 7 shows use of the extracting device 42 to extract the surgical fastener 20 after its deployment as shown in FIG. 6b. This is by way of example only, and the extracting device of the invention may be used to extract any surgical fastener having a crown and baseplate provided that a filament was inserted between the crown and baseplate prior to deployment in such a way that the filament becomes pinched and immobilized between the crown and baseplate after deployment. In FIG. 7a, a user 70 has grasped the extracting device 42 in one hand and has grasped the filament 62 with his or her other hand, with the gap 60 of the ring element 52 in register with the longitudinal groove 49 of the cylindrical element 58. The filament 62 and the device 42 are then manipulated so as to insert the filament into the longitudinal groove 49 (FIG. 7b). The ring element 52 is then rotated into its position in which the gap 60 is not in register with the groove 49 (FIG. 7c). In this configuration, the filament 62 is prevented from escaping from the groove 49. Then, as shown in FIG. 7d, the extraction device is moved towards the tissue and applied to the fastener. The filament 62 is then pulled away from the tissue surface 33 of the body tissue 34. As the filament 62 is pulled away, the crown 22 of the fastener 20 enters into the interior of the cylindrical element 58. The cylindrical element 58 has a lumen having a cross-sectional shape and dimensions that allow the crown to enter the lumen, while the baseplate is prevented from entering the lumen. Thus, as the filament 62 continues to be pulled away from the tissue surface 33, the crown 22 is pulled by the filament 62 into the interior of the cylindrical element 58 while movement of the baseplate 24 is arrested when the baseplate 24 contacts the distal end of the cylindrical element 58, as shown in FIG. 7e. As the crown 22 moves away from the baseplate 24, the prongs 26 slide through the slots 32 until the tips 28 of the prongs 26 are at or near the tissue surface 33. The extraction device 42, with the fastener 20 firmly held at the distal end of the cylindrical element by the pulled filament 62 is then removed from the body.

The invention claimed is:

1. A method for extracting a deployed surgical fastener form a body tissue, the surgical fastener having a crown, a baseplate and prongs extending from the crown, the surgical fastener having an undeployed configuration in which the crown is separated from the baseplate by a first distance and a deployed configuration in which the crown is separated from the baseplate by a second distance that is less than the first distance, the method comprising:

(a) providing an extracting device, the extracting device comprising a shaft having a proximal end and a distal end, at least a distal portion of the shaft having a lumen with a cross-sectional shape and dimensions to allow the crown of the surgical fastener to enter the lumen while preventing the baseplate of the surgical fastener from entering the lumen, the shaft of the extraction device comprises
a sheath;
a rod; and
a hook located at the distal end of the rod, the rod being slidable in the sheath between a retracted position in which the hook is retracted into the distal end of the sheath and an extended position in which the hook extends beyond the distal end of the sheath, and
wherein the hook comprises a flat top surface and a flat bottom surface, the top and bottom surfaces being substantially perpendicular to a direction of movement of the hook when the hook moves between the retracted position and the extended position;

(b) introducing the crown into the lumen while preventing the advancement of the baseplate by the distal part of the shaft;

(c) bringing the rod to its extended position;

(d) inserting the hook between the crown and the baseplate of the fastener; and (e) bring the rod to its retracted position.

2. The method according to claim 1 wherein the rod is spring biased in the extended position.

* * * * *